(12) United States Patent
Shimizu et al.

(10) Patent No.: US 9,227,011 B2
(45) Date of Patent: Jan. 5, 2016

(54) MINIATURIZED THRESHOLD SENSOR

(75) Inventors: Jeff Shimizu, Cortlandt Manor, NY (US); Hans Zou, Windsor, NJ (US); Johan Frederik Dijksman, Weert (NL); Anke Pierik, Eindhoven (NL); Judith Margaret Rensen, Eindhoven (NL)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 239 days.

(21) Appl. No.: 12/442,961

(22) PCT Filed: Sep. 27, 2007

(86) PCT No.: PCT/IB2007/053931
§ 371 (c)(1),
(2), (4) Date: Mar. 26, 2009

(87) PCT Pub. No.: WO2008/038246
PCT Pub. Date: Apr. 3, 2008

(65) Prior Publication Data
US 2010/0033324 A1    Feb. 11, 2010

Related U.S. Application Data

(60) Provisional application No. 60/827,488, filed on Sep. 29, 2006.

(51) Int. Cl.
*G08B 1/08* (2006.01)
*A61M 5/142* (2006.01)
(Continued)

(52) U.S. Cl.
CPC ............ *A61M 5/14276* (2013.01); *A61B 5/073* (2013.01); *A61M 5/1723* (2013.01); *A61B 2562/0214* (2013.01); *A61M 2005/1726* (2013.01); *A61M 2210/1053* (2013.01)

(58) Field of Classification Search
CPC .... A61B 5/0031; A61B 5/073; A61B 5/0022; A61B 5/00016; A61B 5/4081; A61B 5/6861; A61B 5/686; A61B 1/00032; A61N 1/05; A61J 3/007
USPC .................. 340/561, 562; 600/300, 333, 535; 607/12
See application file for complete search history.

(56) References Cited

U.S. PATENT DOCUMENTS 1,828,777 A    10/1931    Leventhal
2,027,663 A     1/1936    Allyn
(Continued)

FOREIGN PATENT DOCUMENTS

EP    1215485 A1    6/2002
JP    2002-228616 A    8/2002
(Continued)

OTHER PUBLICATIONS

Gallardo-Soto et al, "Near Patient Testing: Diagnosing a First World Killer", TCE, 732, Aug. 2002, pp. 30-32.
(Continued)

*Primary Examiner* — Travis Hunnings
(74) *Attorney, Agent, or Firm* — Lee & Hayes, PLLC

(57) ABSTRACT

A sensor comprising a plurality of electrodes having a miniature size and a lower power consumption and a coating exterior to the electrodes, wherein the coating interacts with a target condition thereby producing a change in an electrical property of the electrodes, wherein the change is transduced into an electrical signal by the electrodes. Further a system for medication delivery comprising such sensor and a pill.

15 Claims, 1 Drawing Sheet

(51) Int. Cl.
  *A61B 5/07* (2006.01)
  *A61M 5/172* (2006.01)

(56) References Cited

U.S. PATENT DOCUMENTS

| | | | |
|---|---|---|---|
| 2,230,866 A | 9/1967 | Noller | |
| 3,340,866 A | 9/1967 | Noller | |
| 3,719,183 A | 3/1973 | Schwartz | |
| 4,589,418 A * | 5/1986 | Gopikanth | 600/361 |
| 5,571,698 A | 11/1996 | Ladner et al. | |
| 5,846,744 A | 12/1998 | Athey et al. | |
| 5,914,381 A * | 6/1999 | Terado et al. | 527/300 |
| 6,103,865 A | 8/2000 | Bae et al. | |
| 6,402,689 B1 * | 6/2002 | Scarantino et al. | 600/300 |
| 6,929,636 B1 | 8/2005 | Von Alten | |
| 8,847,766 B2 * | 9/2014 | Zdeblick et al. | 340/573.1 |
| 2001/0026807 A1 | 10/2001 | Watts | |
| 2002/0119176 A1 | 8/2002 | Greenberg et al. | |
| 2002/0132226 A1 | 9/2002 | Nair et al. | |
| 2004/0147969 A1 * | 7/2004 | Mann et al. | 607/17 |
| 2004/0153270 A1 | 8/2004 | Yamashita et al. | |
| 2005/0123680 A1 | 6/2005 | Kang et al. | |
| 2006/0137984 A1 | 6/2006 | Gumbrecht et al. | |
| 2006/0155174 A1 | 7/2006 | Glukhovsky et al. | |
| 2006/0276844 A1 * | 12/2006 | Alon et al. | 607/2 |
| 2009/0234331 A1 * | 9/2009 | Langereis et al. | 604/891.1 |

FOREIGN PATENT DOCUMENTS

| | | | |
|---|---|---|---|
| JP | 2004-516889 A | 6/2004 | |
| JP | 2004538055 | 12/2004 | |
| JP | 2005-334331 A | 12/2005 | |
| JP | 2006-510882 A | 3/2006 | |
| WO | 0010007 A2 | 2/2000 | |
| WO | 02/07598 A1 | 1/2002 | |
| WO | WO 0207598 A1 * | 1/2002 | |
| WO | WO2004030652 | 4/2004 | |
| WO | 2004/046704 A1 | 6/2004 | |
| WO | 2004/057335 A1 | 7/2004 | |
| WO | 2004066903 A2 | 8/2004 | |
| WO | 2006021932 A1 | 3/2006 | |
| WO | WO2006050098 | 5/2006 | |
| WO | WO2006056944 | 6/2006 | |

OTHER PUBLICATIONS

Ravi et al, "Fabrication of Symmetrical Section Microfeatures Using the Electro-Discharge Machining Block Electrode Method", Journal of Micromechanics and Microengineering, vol. 12, 2002, pp. 905-910.

Masuzawa, "State of the Art of Micromachining", CIPR, vol. 49, 2000, pp. 473-488.

Hoffman, "Bioconjugates of Intelligent Polymers and Recognition Proteins for Use in Diagnostics and Affinity Separations", Clinical Chemistry, vol. 46, No. 9, 2000, pp. 1478-1486.

Siegel et al, "PH-Dependent Equilibrium Swelling Properties of Hydrophobic Polyelectrolyte Copolymer Gels", Macromolecules, 21, 1988, pp. 3254-3259.

Mc Neil et al, "Electrochemical Sensors Based on Impedance Measurement of Enzyme-Catalyzed Polymer Dissolution: Theory and Applications" Anal. Chem, 1995, 67, pp. 3928-3935.

Allen, "Micro-Electrodischarge Machining", 1997 IEE Colloquium on Recent Advances in Micromachining Techniques (IEE Colloquium Digest No. 1997/081).

Tanaka, "Collapse of Gels and the Critical Endpoint", Phys. Rev. Lett. 40, 820-923, 1978.

Office Action dated Jul. 3, 2012 in corresponding Japanese Patent Application No. 2009-529837, including English translation provided by ITOH International Patent Office.

The Chinese Office Action mailed Apr. 22, 2013 for Chinese patent application No. 200780036417.1, a counterpart foreign application of U.S. Appl. No. 12/442,961, 12 pages.

The Japanses Office Action mailed Jul. 18,2013 for Japanese patent application No. 2009-529837, a counterpart foreign application of U.S. Appl. No. 12/442,961, 6 pages.

The European Office Action mailed Sep. 30, 2014 for European patent application No. 07826565.9, a counterpart foreign application of U.S. Appl. No. 12/442,961, 4 pages.

Fernandez-Sanchez, et al., "Electrochemical impedance spectroscopy studies of polymer degradation: application to biosensor development", Trends in Analytical Chemistry, vol. 24, No. 1, 2005, 12 pages.

The Japanese Office Action mailed Feb. 10, 2015 for Japanese patent application No. 2009-529837, a counterpart foreign application of U.S. Appl. No. 12/442,961, 37 pages.

\* cited by examiner

MINIATURIZED THRESHOLD SENSOR

This application relates generally to methods, systems, and articles of manufacture for a sensor for detecting a target condition.

A sensor is a device that detects a substance of interest and/or measures a concentration of the substance. A biosensor, in particular, uses bio-mimetics or biological materials such as tissues, microorganisms, organelles, cell receptors, enzymes, antibodies, or nucleic acids and a physicochemical detector, such as an electrode. Physicochemical detectors used in biosensors are exemplified by the following types: optical, piezoelectric, electrochemical, thermometric, or magnetic.

Sensors have been used for a variety of applications, including medical uses such as measurement of a concentration of blood glucose or one or more other blood-borne substances in a sample of blood. Sensors further have environmental and industrial uses, for example, detecting toxic materials, contaminants, pathogenic organisms, and other unwanted or foreign materials.

A sensor used for ex vivo detection of blood-borne markers of acute myocardial infarction, especially fatty acid binding protein (FABP), is described in Gallardo-Soto et al. A sample of blood is collected and placed into contact with the sensor, which includes electrodes that have a coating (tce, 732, August 2002, pp. 30-32). If present in sufficient concentration, FABP degrades the coating, resulting in a change in impedance at a surface of the electrodes. A value of the change in impedance is used to calculate concentration of FABP in the sample.

Further, a sensor for ex vivo measurement of concentration of an analyte in an ex vivo sample of whole blood, serum, plasma, urine, or saliva is described in U.S. Pat. No. 5,846,744.

Accordingly, one embodiment herein is a sensor including a plurality of electrodes having a miniature size and a low power consumption; and a coating exterior to the electrodes and interacting with a target condition in order to produce a change in at least one of a physical property, an electrical property, and a chemical property at a surface of the electrodes, in which the change is transduced into an electrical signal by the electrodes.

The sensor is usable in a cavity. A "cavity," as used herein, refers to a small space within a naturally occurring or artificial structure. For example, a cavity can include a region beneath a surface of earth, a region within an architectural structure, a region within an apparatus, a region within a body (i.e., a bodily cavity), or a region within a fluid environment, for example a liquid environment, an aerial environment, or a plasmatic environment. A cavity, as used herein, includes a region receiving a sensor. The cavity may be chosen from among: an architectural site, a subterranean site, a hydric site, an aerial site, an agricultural site, and a naturally occurring site.

A "bodily cavity," as used herein, refers to a space within a body of an animal, for example, a gastrointestinal (GI) tract, a peritoneal cavity, an abdominal cavity, a cerebrospinal space, a lung, a uro-genital cavity, an intracranial site, a subcutaneous site, an intramuscular site, or a vascular tract within a mammal, for example, a human. A bodily cavity also includes regions within the body or tissue of nonliving animals, for example, cadavers, or portions of non-living tissue, such as meat or meat products. A bodily cavity, as used herein, includes a region receiving a sensor, such as subcutaneous insertion.

Low power consumption is for example at least about 0.1 µwatts to about 10 µwatts. However, the power consumption may also be less than about 50 µwatts to about 1,000 µwatts.

The coating may include a pH-sensitive polymer.

The coating may also include a hydrogel and an interaction between the hydrogel and the target condition alters hydration of the hydrogel.

The target condition includes, for example, a presence of at least one of the following substances: blood, inflammatory agents, enzymes, hydrogen ions, and hydroxyl radicals.

A change in electrical property, for example, includes a change in capacitance. The change in capacitance may be detected, for example, by measuring at least one parameter selected from the group consisting of: current, potential, and impedance.

Another related embodiment provides the sensor used in conjunction with a pill, in which the sensor and the pill form a sensor apparatus.

Another embodiment is a method for using a sensor apparatus that includes a sensor and a pill to deliver a composition into a cavity, the method including: inserting the apparatus into the cavity, in which the sensor provides a plurality of electrodes having a miniature size and a low power consumption and a coating exterior to the electrodes and in which the pill provides a reservoir of a composition, a pump, and electronics, in which electronics contain at least one circuit; detecting a target condition, in which the target condition interacts with the coating to produce a change in at least one of the following properties: a physical property, an electrical property, and a chemical property, in which the change occurs at a surface of the electrodes and the sensor transduces the change into an electrical signal and the signal is detected by the at least one circuit; and dispensing the composition at a target location, in which the composition is held in the reservoir and is delivered using the pump, in order to use the sensor apparatus that includes the sensor and a pill to deliver the composition into the cavity.

The apparatus is usable in a bodily cavity, wherein the bodily cavity is, for example, selected from the group consisting of: a gastrointestinal tract, a peritoneal cavity, an abdominal cavity, a cerebrospinal space, a lung, a uro-genital cavity, and a vascular tract.

Detecting the target condition may further include comparing the change to a stored threshold value.

The coating, for example, includes a pH-sensitive polymer or a hydrogel and an interaction between the hydrogel and the target condition alters hydration of the hydrogel.

The change in electrical property may include a change in capacitance. The change in capacitance is detected, for example, by measuring at least one of the following parameters: current, potential, and impedance.

Another embodiment is a system for delivering a composition into a cavity, the system providing: a sensor apparatus that includes a sensor and a pill, in which the sensor includes a plurality of electrodes of miniature size and low power consumption and a coating exterior to the electrodes, and in which the pill provides: a battery, a reservoir of a composition, a pump, and electronics, in which electronics contain at least one circuit and in which the electrodes of the sensor are connected to the electronics of the pill, in order to control at least one of a timing and a placement of delivery of the composition; and a target condition in a cavity, in which the target condition interacts with the coating exterior to the electrodes, an interaction producing a change in at least one physical property or chemical property at a surface of the electrodes, in which the change is transduced by the electrodes and detected by the at least one circuit.

In an exemplary embodiment, the sensor provided herein is used with a pill to mediate an action such as a delivery of a medication, for example, a controlled-release delivery of a medication.

The pill provided herein, is an ingestible device or an implantable device that has a chemically resistant outer shell. The pill has a variety of applications, for example, determining medical information for diagnosis of diseases such as Crohn's disease, celiac disease, small bowel tumors, and gastroparesis.

Existing sensors for ex vivo laboratory analysis or biological assay of a collected sample are not adapted for use in vivo. Further, current sensors are not adapted for use in vivo with a pill, for example, for a delivery of a medication in a GI tract, by not having advantages of the devices provided herein, for example, a small size and/or a low power consumption.

For application to a pill, the sensor operates in vivo, for example, in a GI tract, and in a very small volume. Thus, the sensor is miniature in size, and has low power consumption.

The term "in vivo," as used herein, refers to a region within a body of an animal, for example, within a bodily cavity, for example of a human body. The term "ex vivo," as used herein, refers to a location that is not within a body or a bodily cavity.

A "miniature size," as used herein, refers to a size that is smaller than that of devices used or described in the past. For example, a sensor for ex vivo use that is about 10 mm in diameter is described in U.S. Pat. No. 5,846,744, whereas the plurality of electrodes of the present claims are, for example, less than about 1 mm, or less than about 0.5 mm, or less than about 0.2 mm, or less than about 100 μmeters, or less than about 50 μmeters, or less than about 10 μmeters, or less than about 5 μmeters.

As used herein, "low power consumption" refers to consumption of less power than devices described in the prior art. The sensor disclosed herein has low power consumption, for example, of a few microwatts. Thus, the power consumption is less than 100 microwatts, less than 50 microwatts, or less than 10 microwatts, due to having a miniature size and performing simple measurements, for example, measurements of impedance.

The sensor provided herein is, for example, a biosensor. That is, the sensor includes, for example, a use of bio-mimetics or biological materials such as enzymes, and a physicochemical detector, such as an electrode.

Figure 1:
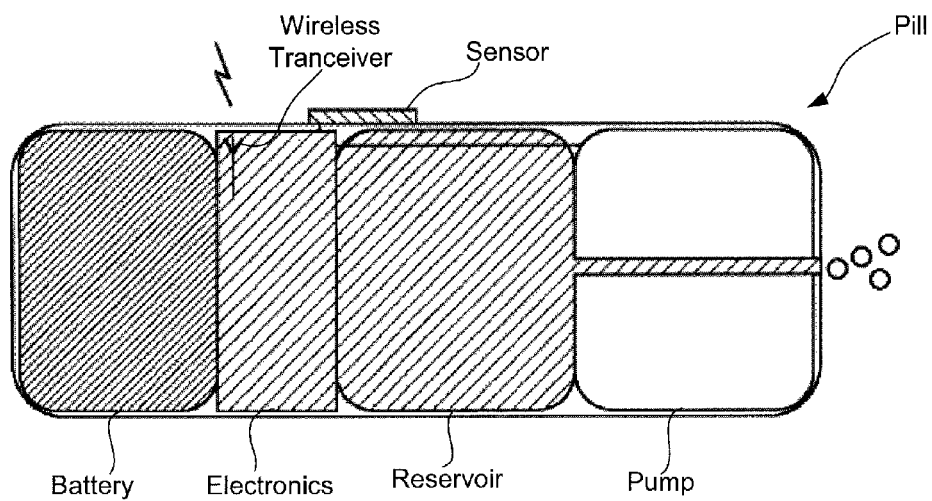
FIG. 1 shows a sensor and a pill containing a battery, electronics including a micro-controller transceiver for communication, a drug reservoir, and a pump.

An exemplary embodiment of the device provided herein is shown in FIG. 1. A sensor containing electrodes is attached to or placed on an exterior surface of pill. Electrical contact is made between the electrodes and electronic circuitry inside the pill. The pill contains a battery, electronics, a reservoir of medication (identified as Drug Reservoir in FIG. 1) and a pump. The pill optionally has a wireless transceiver for communication with a user. Pill contents are contained in a shell that protects pill components from an environment in the cavity, for example in a bodily cavity of a patient, and isolates the device to protect the patient from pill contents.

The shell of the pill is made of a sealed, biocompatible material, for example, a material that is resistant to digestive fluids. Further, the shell is shaped for passage through the GI tract. The shell has a small size and/or a small thickness, for example, for passage through the GI tract.

A sensor apparatus is used for a delivery of medication in a GI tract. The sensor apparatus is connected to the pill, which is swallowed by a patient. The apparatus is propelled through the alimentary canal by natural contractions, called peristalsis.

The term "sensor apparatus" as used herein includes a sensor and a pill, in which the sensor is connected to, attached to, or otherwise placed in physical contact with the pill. In an exemplary embodiment, the sensor is located exterior to the shell of the pill.

The pill is capable of producing an action, for example a delivery of medication, in response to measurements of an environment, for example, an environment inside a body of a patient. The sensor is capable of indicating a value of pH in the environment, for example, by transducing a change in a coating exterior to electrodes of the sensor. The value of the pH further indicates position of the pill in a GI tract, as ranges of values of pH at various locations in a GI tract are known. For example, the pH of the GI tract steadily increases as a function of length, from a pH of about 5.0 to a pH of about 6.5 in the jejunum, from a pH of about 6.0 to a pH of about 7.5 in the ileum, and from a pH of about 6.0 to a pH of about 8.0 in the colon. During transit of a sensor through the GI tract, values of pH rise quickly upon exiting the stomach and steadily rise, more slowly, as the sensor progresses through the small intestines and colon. In some embodiments, the pill uses indications of location based on pH to deliver medication at a target location.

A "target condition," as used herein, refers to a presence of an amount of, or a value of, a substance of interest. A "target location," as used herein, refers to a location of a target condition within a cavity. The target location is, for example, a site of a delivery of a medication. For example, for the delivery of the medication to the colon, the colon is the target location. The target location, for example the colon, is indicated by a target condition, for example a value of pH corresponding to a location in the colon.

The devices provided herein do not require a preparation of a sample for analysis. Rather, electrodes having an exterior coating are exposed to an environment and transduce changes in the coating, for example a degradation of the coating, or a corresponding chemical change and/or electrical change, for example a change in capacitance, into an electrical signal. The signal is received by circuitry within the pill. When a degree of a change in a coating or a corresponding chemical change or electrical change exceeds a threshold value, electrodes of the sensor produce an electrical signal that indicates that an action is appropriate, for example, a delivery of a medication from the reservoir located within the pill.

Circuitry within the pill stores data, obtains new data received from the sensor as a function of time and updates the stored data related to desired parameters relevant to the function. Exemplary parameters include release profile and pill behavior. The circuitry further regulates the pill for the purpose of dispensing medication from the reservoir by using the pump. The circuitry further optionally includes a transceiver for communication with a user. Thus, pre-set programming is used in conjunction with signals received from the sensor and/or from wireless communication.

Each sensor includes one or more electrodes, for example, two electrodes. Methods of fabricating electrodes, for example microelectrodes, are well known to those skilled in the art, and include a wire electro-discharge grinding (WEDG) method, a mesh electrode method, a lithography, electroplating, and molding (LIGA) method, a micromechanical machining method and especially an electro-discharge machining block electrode method. See Ravi et al., J. Micromech. Microeng. 12 (2002) 905-910; Masuzawa, Ann. CIPR 49 (2000) 473-88; Allen, Proc. 1997 IEE Colloquium on Recent Advances in Micromachining Techniques (IEE Colloquium Digest No 1997/081).

Each electrode has an exterior coating. The coating of the sensor, for example a polymer coating, is pre-selected by a user for having one or more desired chemical or physical characteristics, according to a target condition or target location of interest. For example, for detecting a target location which is a jejunum, a polymer is pre-selected to be pH-sensitive and to degrade or interact otherwise at a pH of about 5.0.

Some polymer coatings, for example enteric coatings, are pH-sensitive and respond by degrading or by altering otherwise at a selected pH. Degradation of a polymer coating can indicate that the pill has encountered a target condition or a target location in vivo.

Methods of making and selecting responsive polymers are well known in the art, and are described in Hoffman, *Clinical Chemistry* 46(9): 1478-1486 (2000), which is incorporated herein by reference. Exemplary forms of synthetic responsive polymers includes EUDRAGIT® polymers, which are a class of degradable compounds including synthetic polymers of methacrylate, methacrylic acid, and ethylmethacrylate, which are commercially available (Degussa, Darmstadt, Germany). Other exemplary coatings, including pH-sensitive coatings, enzymatic coatings, and several other dissolvable coatings are described in the Encyclopedia of Controlled Drug Delivery, John Wiley & Sons, 1999 (for example, pp. 299-311), which is incorporated herein by reference.

Other examples of coatings include for example, enzymatic or acidic coatings, used to detect specific substances of interest. For example, coatings that degrade in a presence of an azoreductase are well known and provide an indication that the pill has entered the colon. Presence and activity of azoreductase enzymes, a class of bacterial enzymes that reduce azo bonds, have commonly been exploited for use in mechanisms for controlled-release delivery of medication. (See the Encyclopedia of Controlled Drug Delivery, John Wiley & Sons, 1999, incorporated herein by reference; see pp. 717-726.)

Another example of a coating is a coating of polymeric hyaluronic acid used to detect a presence of hydroxyl radicals produced by phagocytic cells. A coating of hyaluronic acid degrades or otherwise interacts in the presence of hydroxyl radicals. Other exemplary polymer coatings respond to a presence of blood or inflammatory markers such as cytokines. Cytokines are proteinaceous signaling compounds that are involved in intercellular communication in a variety of immunological, inflammatory and infectious biological processes. Cytokines can be detected by including in the coating an antibody or a binding protein that interacts specifically with the cytokine of interest. See Ladner et al., U.S. Pat. No. 5,571,698, incorporated herein by reference.

In an alternative embodiment, electrodes are coated with a responsive hydrogel that can be of synthetic or naturally-occurring origin, or can be derived from a naturally-occurring polymer. A hydrogel is a colloidal network of polymers dispersed in water. A colloid is formed when a substance having a certain physical phase (e.g. gas, liquid, or solid) is dispersed in another substance with the same or a different physical phase. A responsive hydrogel responds to a target condition by increasing or decreasing a value of its hydration. Responsive hydrogels, for example hydrogels that are responsive to pH, are well known to those skilled in the art of biochemistry. See, for example, Tanaka, T. Collapse of gels and the critical endpoint. Phys. Rev. Lett. 40, 820-823 (1978). Siegel, R. A. & Firestone, B. A. pH-dependent equilibrium swelling properties of hydrophobic polyelectrolyte copolymer gels. Macromolecules 21, 3254-3259 (1988), which are incorporated herein by reference.

Well-known examples of hydrogels include aqueous cooled solutions of any of the biologically synthesized polymers including agar, gelatin, or starch that have been dissolved in aqueous solution at a higher temperature and then cooled to form a gel. Examples of synthetic hydrogels include aqueous cooled solutions of copolymers of N-isopropylacrylamide and acrylic acid that have been dissolved at a higher temperature and then cooled to form a gel.

Advantages of hydrogels include that hydrogels do not degrade, and that a state of hydration of the hydrogel is reversible. Electrodes having an exterior coating of hydrogel also may have an ability to detect multiple targets during a course of transit through a GI tract.

The sensor operates, for example, as two electrodes connected electronically together to form a capacitor. A coating that is exterior to the electrodes acts as a dielectric. In response to a presence of or a value of a target condition, one or more characteristics of the coating are altered. For example, a degradable coating degrades or a hydrogel increases in volume. As one or more characteristics of the coating are altered, a change is produced in a value of a dielectric constant, resulting in a change in a value of capacitance. A standard model for capacitance of a sensor of two electrodes is based on a well-known formula for capacitance of a parallel plate capacitor having two parallel plates:

$$C = (\epsilon_0 * \epsilon_r * A)/d, \text{ in which}$$

$\epsilon_0$ is a constant representing permittivity of free space, $\epsilon_r$ is a dielectric constant, which varies according to the composition and thickness of the dielectric, A is a surface area of a parallel plate that is contacted if the distance between two parallel plates is equal to zero (in this case, A corresponds to a surface area of the broadest and flattest surface of an electrode), and d is a distance between the two parallel plates (in this case, the distance between the two electrodes).

When a change at the surface of the electrodes, for example a change in capacitance corresponding to coating degradation or change in hydration of a hydrogel, exceeds a predetermined threshold amount, the sensor indicates a positive signal to the pill, which produces an event, for example delivery of a composition, or for example delivery of medication from the reservoir within the pill.

A change in capacitance is detected by measuring impedance, electric current, and/or electric potential. The sensor obtains a measurement, for example, a measurement of impedance, periodically, for example about every few seconds or about every few tens of seconds or about every few minutes or every few hours. Electrodes of a sensor transduce a change occurring at an electrode surface, for example a change in capacitance, into an electrical signal, which is detected by the circuitry of the pill using a simple direct electrical connection.

Methods of calculating impedance of an electrode are described in McNeil *Anal. Chem.* 1995, 67, 3928-3935, which is incorporated herein by reference. Capacitance is a well-known electrical measure of the amount of electric charge stored at a given electric potential between any two conductors that are insulated from one another; electric current is a well-known electrical measure of the flow of electric charge per unit time; electric potential, typically measured in volts, is a well-known electrical measure of potential energy per unit of electric charge in a static electric field; and impedance is a well-known electrical measure of total opposition to flow of sinusoidal (alternating) electric current.

Figure 2:
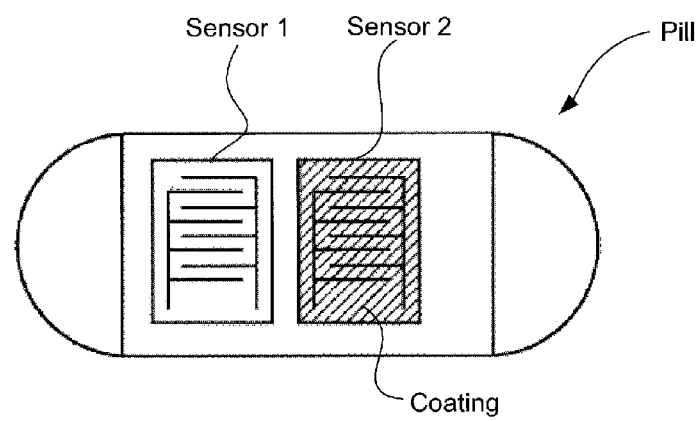
FIG. 2 shows a pill and two sensors.

In another embodiment illustrated in FIG. 2, a plurality of sensors is used. A diagram of a pill and two sensors is shown in FIG. 2. In this exemplary embodiment, electrodes are placed on an exterior surface of the pill and electrical contacts are made between the electrodes and the electronic circuitry within the pill. Electrodes of each sensor have a pre-selected exterior coating. The electrodes of each individual sensor optionally have an exterior coating of a reactive polymer that is unique to that sensor. For example, electrodes of a first sensor have an exterior first coating, for example, a coating that degrades only at a pH greater than 4, and electrodes of second sensor have an exterior second coating, for example, a coating that degrades only at a pH greater than 6.5. Thus, location of the pill may be determined using measurements of pH and known values of pH in various locations within the GI tract.

The sensors provided herein have many additional applications, both within the field of medicine and in other fields, such as for example use with a fluid delivery device, use with an implantable device, and use with a drug delivery device, within a bodily cavity. The sensor may also have dental and veterinary applications or be used for other applications to detect a target condition, for example, for environmental, agricultural, and industrial applications, such as detecting pesticides, insecticides, herbicides, chemicals including sewage and/or petrochemicals, and other water contaminants in rivers and water treatment facilities; detecting toxic substances before and after bioremediation; detecting pathogens, for example remote sensing of airborne viruses, bacteria, or bacterial spores for counter-bioterrorist activities; detecting structural abnormalities beneath buildings and other structures; detecting microbes in biomass or in a biome; and detecting microorganisms in food products such as milk or meat.

It will furthermore be apparent that other and further forms of the invention, and embodiments other than the specific and exemplary embodiments described above and in the claims, may be devised without departing from the spirit and scope of the appended claims and their equivalents, and therefore it is intended that the scope of this invention encompasses these equivalents and that the description and claims are intended to be exemplary and should not be construed as further limiting.

What is claimed is:

1. An electronic pill comprising:
   a capsule configured for placement in a bodily cavity;
   a reservoir disposed in the capsule and containing a composition;
   a pump disposed in the capsule and configured for pumping the composition contained in the reservoir outside the capsule;
   a sensor comprising first and second electrodes disposed on a surface of the capsule and being connected electronically together to form a capacitor; and a polymer coating covering each of the first and second electrodes and acting as a dielectric on the capacitor; and
   electronics including at least one circuit connecting the pump and the sensor, wherein:
   contact of the polymer coating by a predetermined target condition in the bodily cavity causes the polymer coating to dissolve, dissolution of the polymer coating changes a value of a dielectric constant, the change in the value of the dielectric constant changes a capacitance of the capacitor, the change in the capacitance of the capacitor is detected as an electrical signal, and the electrical signal signals the pump to pump the composition out of the reservoir into the bodily cavity.

2. The electronic pill according to claim 1, wherein the bodily cavity is selected from the group consisting of: a gastrointestinal tract, a peritoneal cavity, an abdominal cavity, a cerebrospinal space, a lung, a uro-genital cavity, a vascular tract, a subcutaneous site, and an intramuscular site.

3. The electronic pill according to claim 1, wherein the sensor has a low power consumption of at least about 0.1 µwatts to about 10 µwatts.

4. The electronic pill according to claim 1, wherein the sensor has a low power consumption of less than about 50 µwatts to about 1,000 µwatts.

5. The electronic pill according to claim 1, wherein the coating comprises a pH-sensitive polymer and the target condition comprises a predefined pH.

6. The electronic pill according to claim 1, wherein the target condition comprises at least one of blood, inflammatory agents, enzymes, hydrogen ions, and hydroxyl radicals.

7. The electronic pill according to claim 1, wherein the change in capacitance is detected by measuring at least one of current, potential, and impedance.

8. A method of delivering a composition into the alimentary canal comprising:
   providing a sensor apparatus comprising a sensor integrated with a capsule, wherein the sensor comprises a plurality of electrically-connected electrodes formed as a capacitor and a polymeric coating covering the selected to dissolve in the presence of a target condition in the alimentary canal, and wherein the capsule comprises a reservoir containing a composition, a pump, and electronics including at least one circuit connecting the sensor and the pump, wherein:
   the capsule is swallowed and traverses the alimentary canal,
   presence of the target condition causes dissolution of the coating,
   the sensor transduces the dissolution of the coating into an electrical signal detected by the at least one circuit, and
   the electrical signal signals the pump to pump the composition out of the reservoir into the alimentary canal, and
   the pump pumps the composition in response to the electrical signal.

9. The method according to claim 8, wherein the apparatus is used in a bodily cavity.

10. The method according to claim 8, wherein the cavity is selected from the group consisting of: a gastrointestinal tract, a peritoneal cavity, an abdominal cavity, a cerebrospinal space, a lung, a uro-genital cavity, and a vascular tract.

11. The method according to claim 8, wherein detecting the target condition further comprises comparing the change to a stored threshold value.

12. The method according to claim 8, wherein the coating comprises a pH-sensitive polymer.

13. The method according to claim 8, wherein the dissolution of the coating produces a change in capacitance.

14. The method according to claim 13, wherein the change in capacitance is detected by measuring at least one of current, potential, and impedance.

15. A system for delivering a composition into a cavity, the system comprising:
   a sensor apparatus comprising a sensor and a pill, wherein the sensor further comprises a plurality of electrodes of miniature size and low power consumption forming a capacitor and a polymer coating covering the electrodes forming a dielectric, and wherein the pill further comprises:
a battery,
a reservoir containing of a composition,
a pump, and
electronics, wherein the electronics contain at least one circuit and a transceiver, and wherein the electrodes of the sensor make a connection to the electronics of the pill, thereby controlling at least one of a timing and a placement of delivery of the composition; and
wherein contacting the sensor with a fluid in the cavity having a pre-determined pH level causes a dissolution of the coating on the electrodes, the dissolution of the coating on the electrodes causes a change in a dielectric constant, the change in the dielectric constant causes a change in a capacitance of the capacitor, the change in the capacitance is transduced by the electrodes into an electrical signal detected by the electronics, and the electrical signal signals the pump to pump the composition from the reservoir.

* * * * *